United States Patent
Auberger et al.

(12) 
(10) Patent No.: US 6,645,516 B2
(45) Date of Patent: *Nov. 11, 2003

(54) HYDROSOLUBLE COMPOSITION COMPRISING LIPOPHILIC VEGETABLE MATERIAL AND AT LEAST TWO ECOLOGICALLY OPTIMIZED SURFACTANTS

(76) Inventors: Gérard Auberger, 902 route de Raves, 88100 Neuvillers sur Fave (FR); Stéphane Auberger, 902 route de Raves, 88100 Neuvillers sur Fave (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 39 days.

(21) Appl. No.: 09/463,422
(22) PCT Filed: Sep. 20, 1999
(86) PCT No.: PCT/FR99/02229
§ 371 (c)(1), (2), (4) Date: Jan. 21, 2000
(87) PCT Pub. No.: WO00/17294
PCT Pub. Date: Mar. 30, 2000

(65) Prior Publication Data
US 2002/0102281 A1 Aug. 1, 2002

(30) Foreign Application Priority Data
Sep. 21, 1998 (FR) .............................. 98 11833

(51) Int. Cl.⁷ ..................... A01N 25/04; A61K 9/107
(52) U.S. Cl. ................. 424/405; 424/725; 424/731; 514/529; 514/553; 514/558; 514/723; 514/949
(58) Field of Search ................. 424/405, 725, 424/731; 514/724, 553, 529, 772, 783–786, 937, 938, 943, 750, 757, 558, 723; 504/358, 363, 366; 510/437

(56) References Cited

U.S. PATENT DOCUMENTS

| | | | | |
|---|---|---|---|---|
| 5,362,494 A | * | 11/1994 | Zysman et al. | 424/401 |
| 5,594,029 A | * | 1/1997 | Bencsits | 514/552 |
| 5,891,839 A | * | 4/1999 | Erilli et al. | 510/426 |
| 5,922,766 A | * | 7/1999 | Acosta et al. | 514/561 |

FOREIGN PATENT DOCUMENTS

| | | |
|---|---|---|
| DE | 34 32 219 A1 | 3/1986 |
| FR | 2 340 981 | 9/1977 |
| FR | 2 372 226 | 6/1978 |
| FR | 2 663 846 | 1/1992 |
| GB | 2 297 557 A | 8/1996 |

* cited by examiner

*Primary Examiner*—Neil S. Levy
(74) *Attorney, Agent, or Firm*—Davis & Bujold, PLLC

(57) ABSTRACT

The creation of a limpid, stable micro-emulsion from liquid lipophilic materials of vegetable origin, specifically, essential oils, using an ecologically optimized solubilizing agent consisting of a mixture of one ethoxylated vegetable oil and at least one supplemental surfactant comprising an anionic surfactant derived from another vegetable oil and/or a nonionic co-surfactant. The micro-emulsion retains the original active properties of the essential oils in addition to the specific individual properties of the solubilizing agent or the mixture thereof with the lipophilic vegetable materials. Applications: all the applications of essential oils and those conferred by the addition of the specific surfactants.

12 Claims, No Drawings

HYDROSOLUBLE COMPOSITION COMPRISING LIPOPHILIC VEGETABLE MATERIAL AND AT LEAST TWO ECOLOGICALLY OPTIMIZED SURFACTANTS

FIELD OF THE INVENTION

The present invention concerns a hydrosoluble concentrate obtained from a new emulsifying or hydrosolubilizing phase and from a compound of liquid lipophilic materials of vegetable origin, specifically, essential oils or vegetable oils.

Said concentrate is either used directly after dilution with water, or used as an additive or a supplement to various sanitizing, deodorizing, disinfecting, bactericidal, sterilizing, insecticide, biological activator or other product formulations.

BACKGROUND OF THE INVENTION

In the field of emulsifiable concentrates containing liquid lipophilic substances, the use of one or more tensio-actives of vegetable origin with non-biodegradable salts of the sulfate, sulfonate, phosphate type is already known, although phosphorates are harmful to the environment.

Moreover, these preparations result in opaque products that are essentially unstable, making them unsuitable for storage.

Thus, these products are not suitable for many industrial applications.

Inventors have devised a hydrosoluble concentrate obtained from a new emulsifying or hydrosolubilizing phase and from a compound of liquid lipophilic materials of vegetable origin, specifically, essential oils or vegetable oils, in concentrate form which can be used immediately after dilution with water.

The following composition is characteristic of the hydrosoluble or emulsionable concentrate:
- a compound of at least one, but preferably two, liquid lipophilic materials of vegetable origin, specifically essential oils or vegetable oils;
- an emulsifying or hydrosolubilizing mixture containing:
  - a non-ionic tensio-active originating from or deriving from a vegetable oil;
  - at least one non-ionic co-tensio-active and/or another anionic tensio-active originating from or deriving from another vegetable oil;

the combination of which with non-hydrosoluble, liquid lipophilic vegetable materials, specifically, essential oils or vegetable oils, renders the latter completely hydrosoluble or emulsifiable, thereby attaining a total stable micro-emulsion type of emulsion after the addition of water.

The non-ionic tensio-active derived from vegetable oil is preferably an ethoxyl vegetable oil.

Similarly, the supplemental anionic tensio-active is preferably derived from another ethoxyl vegetable oil. For example, it may consist of a mixture of alkyl ethoxyl carboxyl salts resulting from an ethoxylation and carboxylation reaction on the vegetable oils.

SUMMARY OF THE INVENTION

The present invention results from the five following objectives.

The first objective is to avoid denaturing the base properties and qualities of the lipophilic materials, specifically, essential oils or vegetable oils.

The second objective is to furnish a composition with one or more specific properties supplemental to the properties of the liquid lipophilic materials, specifically, the essential oils.

The third objective is to find an especially simple, quick and effective preparation method for emulsifying liquid lipophilic materials of vegetable origin in an aqueous phase in order to obtain a micro-emulsion which will retain the properties and qualities of the original materials in addition to the properties resulting from mixture with the tensio-actives.

The fourth objective is to use at least one tensio-active component of vegetable origin in relatively high proportions in relation to the other tensio-active component or components, the components being used in large quantities in relation to the non-hydrosoluble, liquid lipophilic materials of vegetable origin to impart their own characteristics; the relative weight proportions between the emulsifying or hydrosolubilizing phase and the compound of lipophilic materials of vegetable origin, specifically, essential oils, may be in the range of at least 2 to 1.

The final objective is essentially ecological—to use a low concentration of completely biodegradable vegetable-based substances in a pH-neutral aqueous phase, reflecting absolute and unprecedented concern for environment.

The principal advantage of the invention consists of obtaining simply, quickly, and with maximum efficiency, using liquid lipophilic materials of vegetable origin, i.e., oils known as essential oils or vegetable oils and merely adding water, completely stable micro-emulsions.

A non-exhaustive list of other advantages includes the following:
- an aqueous solution with fluid qualities is obtained, which is transparent, isotropic, and completely stable over time throughout a long storage period, even with considerable variations in ambient temperature or changes in physical-chemical usage conditions;
- faithful conservation of the qualities and properties of the liquid lipophilic materials of vegetable origin, specifically essential oils or vegetable oils, enhanced with supplemental properties (bactericides, bacteriostats, fungicides, antiseptics, deodorants which suppress the cause of bad odors, oxygenator, oxidizers or reductase (s), antiparasitics, insecticides, cleaners and degreasers, etc.) thanks to the encapsulation of the essential oils or vegetable oils by the molecules in the emulsifying or hydrosolubilizing phase described;
- a very low degree of ecotoxicity combined with optimum biodegradability, harmless to humans and animals, due to the use of vegetable-based materials and the appropriate encapsulation of the essential oils or vegetable oils.

In effect, the hydrosolubilizing and emulsifying formulations are biodegradable and the metabolites resulting from the initial decomposition are themselves bio-acceptable, as they are completely biodegradable into natural derivatives. After use, the substance biodegrades in a relatively short period of time from the environmental and ecological point of view.

Furthermore, the formulations are not toxic to ingest, and non-irritating to skin and eyes.
- the micro-emulsion of essential oils or vegetable essences in aqueous phase has considerable wetting, detergent and cleaning power;
- it is particularly simple, effective and quick to use, requiring no expensive equipment and consuming little energy;

DESCRIPTION OF THE PREFERRED EMBODIMENTS

The invention will be described below by using several examples with indications of the proper weight measurements.

EXAMPLE NO. 1

Detergent-Sanitizing Application

An emulsifying or hydrosolubilizing phase is prepared in a container made of chemically inert material by mixing the following components under agitation in the proportions listed:

| | |
|---|---|
| ethoxylated ricinus oil | from 50 to 70% |
| glycol propylene | from 20 to 5% |
| carboxyl ethoxylated alkyl salts | from 10 to 45% |

The salts are the result of an ethoxylating and carboxylating reaction on the vegetable oils.

As a substitute for ricinus oil, any other vegetable oil comprising a free radical (OH) capable of ethoxylation can be used.

After ripening, this emulsified or hydrosolubilizing mixture is incorporated under agitation into a compound of essential oils in the relative proportion of 5% to 30% essential oils to hydrophilize the non-hydrosoluble vegetable materials.

This compound includes several essential oils chosen from the group of rosemary, eucalyptus, mint, cinnamon, pine, artemisia, marjoram, and savory essences.

In order to keep the description complete, an example of the composition by weight is given below:

| | | | |
|---|---|---|---|
| essence of rosemary | 15% | to | 25% |
| essence of eucalyptus | 5% | to | 15% |
| essence of mint | 10% | to | 5% |
| essence of cinnamon | 5% | to | 15% |
| essence of pine | 15% | to | 25% |
| essence of artemisia | 40% | to | 10% |
| essence of marjoram | 5% | to | 3% |
| essence of savory | 5% | to | 2% |

After sufficient agitation, the emulsified concentrate is allowed to rest for 24 hours at ambient temperature, that is, ranging from 150 to 300.

To obtain a completely stable aqueous solution, the emulsified concentrate is next diluted with water in the proportion of 1% to 45% concentrate to 99% to 55% water.

To obtain other physical forms, dilution is considerably less, i.e., from 60% to 20%.

To obtain a flexible gel, the dilution percentage ranges from 1 to 20% water.

To obtain a semi-liquid paste or a viscous liquid, dilution is increased, ranging from 20 to 30% water.

Application No. 2

Deodorizing Application

To the following lipophile phase:
25% compound of essential oils chosen from among essence of orange, essence of lemon, essence of eucalyptus and essence of mint
are added, in a stainless steel container, the following emulsifying phase, which has been previously mixed and ripened:
63% ethoxylated ricinus oil or any other vegetable oil with a free radical (OH) that can be ethoxylated
12% glycol propylene.

This emulsionable or hydrosoluble concentrate is allowed to rest for about 24 hours at ambient temperature.

Next, a small quantity of the emulsionable or hydrosoluble concentrate is added under agitation to water, diluting it in the respective proportions of from 0.5 to 5% concentrate per 99.5% to 95% water.

The deodorizing aqueous solution is immediately ready to use.

An example of the constituents of the lipophilic phase and their minimal weight proportions is given below:

| | | |
|---|---|---|
| essence of orange | at least | 40% |
| essence of lemon | at least | 10% |
| essence of eucalyptus | at least | 8% |
| essence of mint | at least | 1% |

EXAMPLE NO. 3

Biological Activator Application

In a stainless steel container, the following vegetable compound is prepared by mixing:
20% compound of essential oils chosen from among essence of cypress, savory, pine, clove, mint, eucalyptus, rosemary and thyme
10% colza vegetable oil Next, the following is added with care, agitating the mixture regularly
50% ethoxylated ricinus oil or any other vegetable oil with a free radical (OH) that can be ethoxylated;
20% carboxyl ethoxyl alkyl salts resulting from an ethoxylation and carboxylation reaction on vegetable oils.

This emulsifiable or hydrosoluble concentrate is allowed to rest for about 24 hours at ambient temperature.

Next, the emulsifiable or hydrosoluble concentrate is added to water under agitation in a sufficient quantity to result in a dilution ratio of 3% to 45% concentrate per 97% to 55% water.

The fluid aqueous solution with biologically activating properties is ready for use.

With regard to obtaining different physical forms, the dilution percentages are identical to or nearly the same as those indicated previously.

EXAMPLE NO. 4

Insect Repellant Application

In a stainless steel container, the following are added to the lipophilic phase:
25% compound of essential oils chosen from among essences of camphor, lavender, rosemary, citronella, marigold, eucalyptus, carnation, cedar, mint and natural pyrethrum,
the next emulsifying phase which will have been previously mixed and allowed to rest for several hours
63% ethoxylated ricinus oil or any other vegetable oil with a free radical (OH) that can be ethoxylated;
12% glycol propylene.

This emulsifiable or hydrosoluble concentrate is allowed to rest for about 24 hours at ambient temperature.

This emulsifiable or hydrosoluble concentrate is next added to water in a dilution ratio of from 1% to 45% concentrate per 99% to 55% water under agitation to obtain a fluid and limpid aqueous solution that repels insects and which is ready for immediate use.

By way of non-limiting example, the minimum quantities of each of these components is indicated below:

| | | |
|---|---|---|
| essence of eucalyptus | at least | 8% |
| essence of citronella | at least | 8% |
| essence of rosemary | at least | 8% |
| essence of lavender | at least | 10% |
| essence of camphor | at least | 8% |
| essence of pyrethrum | at least | 1% |
| essence of marigold | at least | 10% |
| essence of carnation | at least | 8% |
| essence of cedar | at least | 8% |
| essence of mint | at least | 2% |

Within the realm of this invention, a great number of variations are possible by modifying the composition of the mixture of liquid lipophilic materials of vegetable origin, specifically, essential oils, and the type, the number and proportions of tensio-actives.

Each example listed above describes dilution with a considerable amount of water. As indicated, a small quantity of water can be added if necessary (for example, from 1 to 25% water) to obtain a gel, or a slightly larger quantity of water (for example from about 20% to 30% water) to obtain a semi-liquid paste. This is merely a matter of changes in physical form. More dilution results in an emulsion (for example, using about 30% to 55% water) or a fluid aqueous solution that is isotropic, transparent and clear (for example, using about 55% to 99% water).

What is claimed is:

1. A hydrosoluble micro-emulsion composition comprising:
    water;
    an active liquid lipophilic vegetable material; and
    a hydrosolubilizing phase comprising a mixture of at least two surfactants which are ecologically optimized for reduced ecotoxicity;
    a first surfactant, of the at least two surfactants, being a non-ionic ethoxylated vegetable oil surfactant; and
    a second surfactant, of the at least two surfactants, being an anionic carboxylated ethoxylated vegetable oil surfactant;
    wherein the hydrosolubilizing phase solely hydrosolubilizes the active liquid lipophilic vegetable material, without chemically reacting with the active lipophilic vegetable material, to render the liquid lipophilic vegetable material completely hydrosoluble as a micro-emulsion when mixed with the water, the micro-emulsion is clear and transparent and is substantially harmless to daphnia.

2. The composition according to claim 1, wherein the hydrosoluble composition, when mired with the water, forms a paste or a perfectly limpid and stable micro-emulsion.

3. The composition according to claim 1, wherein the active liquid lipophilic vegetable material contains at least one essential oil.

4. The composition according to claim 1, wherein the non-ionic ethoxylated vegetable oil surfactant is ethoxylated ricinus oil.

5. The composition according to claim 1, wherein the anionic carboxylated ethoxylated vegetable oil surfactant is a mixture of alkyl ethoxyl carboxyl salts resulting from vegetable oils subjected to an ethoxylation and carboxylation reaction.

6. The composition according to claim 1, wherein a relative weight proportion between the hydrosolubilizing phase and the liquid lipophilic vegetable material is at least 2 to 1.

7. A hydrosoluble micro-emulsion composition comprising a mixture of:
    water;
    at least one active liquid lipophilic vegetable material: and
    a hydrosolubilizing phase, the hydrosolubilizing phase comprising:
        a non-ionic ethoxylated vegetable oil surfactant; aid
        an anionic carboxylated ethoxylated vegetable oil surfactant;
    the hydrosoluble composition formed by mixing the hydrosolubilizing phase with the at least one active liquid lipophilic vegetable material so that the hydrosolubilizing phase solely hydrosolubilizes the at least one active liquid lipophilic vegetable material, without chemically reacting with the at least ore active liquid lipophilic vegetable material, rendering the at least one active liquid lipophilic vegetable material completely hydrosoluble in the water and forming the hydrosoluble composition;
    the hydrosoluble composition comprising only vegetable; oil surfactants optimized for ecotoxicity so as to be substantially harmless to daphnia; and
    the hydrosoluble composition being able to form a micro-emulsion when mixed with the water, the micro-emulsion is clear and transparent; and the surfactants are made up exclusively of the elements of oxygen, carbon and hydrogen and the composition biodegrades into the compounds $CO_2$ and $H_2O$.

8. The composition according to claim 7, wherein the hydrosoluble composition, when mixed with the water, forms a paste or a perfectly limpid and stable micro-emulsion.

9. The composition according to claim 7, wherein the active lipophilic vegetable material contains at least one essential oil.

10. The composition according to claim 7, wherein the non-ionic ethoxylated vegetable oil surfactant is ethoxylated ricinus oil.

11. The composition according to claim 7, wherein the anionic carboxylated ethoxylated vegetable oil surfactant is a mixture of alkyl ethoxyl carboxyl salts resulting from vegetable oils subjected to an ethoxylation and carboxylation reaction.

12. The composition according to claim 7, wherein a relative weight proportion between the hydrosolubilizing phase and the liquid lipophilic vegetable material is at least 2 to 1.

* * * * *